United States Patent [19]

Hoekstra

[11] Patent Number: 4,994,618
[45] Date of Patent: Feb. 19, 1991

[54] BEVANTOLOL PREPARATION

[75] Inventor: Marvin S. Hoekstra, Holland, Mich.

[73] Assignee: Warner-Lambert Company, Morris Plains, N.J.

[21] Appl. No.: 243,154

[22] Filed: Sep. 9, 1988

Related U.S. Application Data

[63] Continuation of Ser. No. 610,532, May 15, 1984, abandoned.

[51] Int. Cl.5 ............................................. C07C 93/06
[52] U.S. Cl. .................................................... 564/347
[58] Field of Search ........................................ 564/349

[56] References Cited

U.S. PATENT DOCUMENTS

| | | | |
|---|---|---|---|
| 2,983,757 | 5/1961 | Zaugg | 564/304 |
| 3,033,640 | 5/1962 | Hofer et al. | 564/349 X |
| 3,405,159 | 10/1968 | Krieger et al. | 564/304 X |
| 3,501,769 | 3/1970 | Crowther et al. | 564/349 X |
| 3,857,891 | 12/1974 | Holmes et al. | 564/349 |
| 3,978,127 | 8/1976 | Engelhardt et al. | 564/375 X |
| 4,067,904 | 1/1978 | Comer et al. | 564/349 |
| 4,155,935 | 5/1979 | Yardley et al. | 564/391 X |
| 4,252,984 | 2/1981 | Manoury et al. | 564/349 |

OTHER PUBLICATIONS

Kirk–Othmer "Encyclopedia of Chemical Technology", vol. 6, pp. 484–487 (1955).

*Primary Examiner*—Robert V. Hines
*Attorney, Agent, or Firm*—Ronald A. Daignault

[57] ABSTRACT

The preparation of Bevantolol—i.e., 1-[3,4-dimethoxyphenethylamine]-3-(m-tolyloxy)-2-propanol—is facilitated by contacting the reactants at relatively low temperatures.

1 Claim, No Drawings

BEVANTOLOL PREPARATION

This application is a continuation of application Ser. No. 610,532 filed May 15, 1984, now abandoned.

BACKGROUND

The compound, 1-[3,4-dimethoxyphenethyl)amino]-3-(m-tolyloxy)-2-propanol, Bevantolol, is described and claimed in U.S. Pat. No. 3,857,891. The two methods described in the patent for preparing this compound give low yields; produce undesirable side products; and require the use of prolonged heating and an excess of expensive starting amine reactant for optimum yield. A portion of the excess starting material may be recovered, for example by vacuum distillation, however this procedure is cumbersome and expensive especially when carried out on a large scale, i.e., manufacturing scale.

Bevantolol and derivatives thereof, e.g., acid-addition salts, such as hydrochlorides, are pharmacological agents, exhibiting beta-adrenergic blocking function with cardio-selective activity.

THE INVENTION

It has been discovered that the preparation of Bevantolol (I)

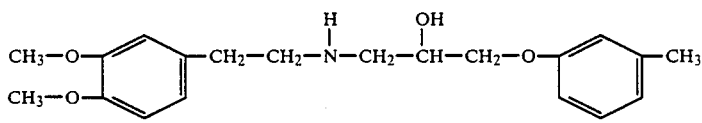

and the subsequent preparation of derivatives thereof can be carried out via the reaction of 3-m-(tolyloxy)-1,2-epoxypropane (II)

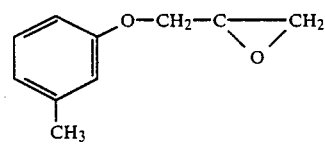

with beta-(3,4-dimethoxyphenyl) ethylamine (III)

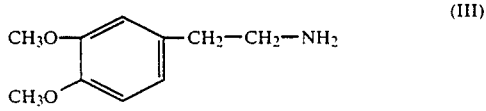

in which the initial contacting of the reactants, compounds II and III, takes place at relatively low temperature, i.e., at a temperature on the order of 0° C. to 25° C., with temperatures of about 5° C. to about 10° highly preferred.

In one embodiment, a two step process is employed. Step 1 involves the production of 3-(m-tolyloxy)-1,2-epoxypropane (II). The preferred method of production in set forth below:

[Step 1]

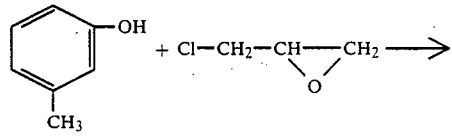

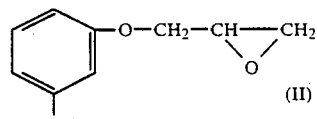

Step 2 involves the reaction of compound II with beta-(3,4-dimethoxyphenyl) ethylamine (III) to yield Bevantolol (I). The principal reaction is:

[Step 2]

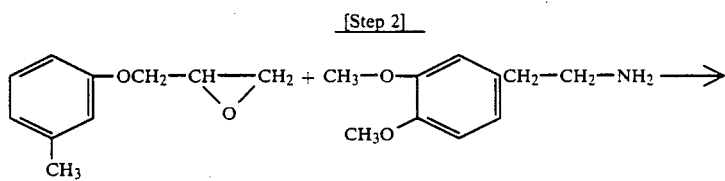

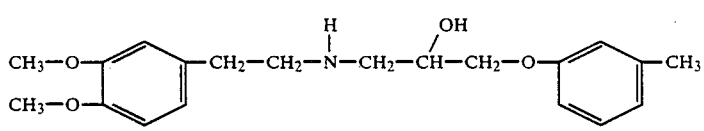

Step 2 takes place at a temperature between about 5° C. and about 10° C.

In this embodiment, the temperature of the amine-epoxide reaction is kept at 10° C. and the mixture is seeded with crystals of Bevantolol base. This causes Bevantolol base to crystallize out of solution upon formation, thus preventing further reaction with the epoxide. After adding hexane and raising the temperature to 25° C. to finish off the reaction, the free base is isolated and converted to Bevantolol hydrochloride in isopropyl alcohol. The overall yield is 78–79%.

ADVANTAGES OF THE INVENTION

The process of the invention has several advantages over known methods of making Bevantolol and derivatives thereof.

Principal among these advantages are:

1. The inventive process gives improved yields or conversion values compared to processes involving the use of reaction temperatures of about 25° C. or more during initial contacting.

2. The instant process uses less energy then conventional processes because prolonged heating is minimized.

3. The new process can be carried out using a primary amine reactant, thereby obviating the need to block the free amino group. Accordingly, there is no need for two or more separate steps which comprise blocking the free amino group with a benzyl group, then removing the benzyl group by, e.g., catalytic reduction. An example of such a removal is the debenzylation of N-benzyl-1-[(3,4-dimethoxyphenethyl)-amino]-3(m-tolyloxy)-2-propanol intermediate.

DESCRIPTION OF THE INVENTION

"Bevantolol" is the United States Adopted Name (USAN) recited in the *United States Pharmacological Dictionary of Druq Names*, 1982, pg. 61, (Mack Printing Company, Easton, Pennsylvania 18042, USA) for the compound 1-[(3,4-dimethoxyphenethyl)amino]-3-(m-tolyloxy) -2-propanol (I)

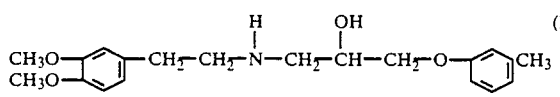

The substituent in the 3-substituted phenoxy group in Bevantolol and its derivatives can be selected from a variety of moieties. Preferred substituents include lower alkoxy, chloro, cyano, hydroxyalkyl (e.g., hydroxymethyl), acyl (e.g., acetyl), m-lower alkyl, or o-vinylic (e.g., allylic) moieties.

Bevantolol and its derivatives are described in U.S. Pat. No. 3,857,891, the disclosure of which is hereby incorporated by reference.

The overall process described herein involves:

(1) contacting compounds II and III at a temperature of 20° C. or less;

(2) adding to the product or step (1) a minor amount of compound I following step (1); and (3) recovering the principal reaction product.

Optionally, the principal reaction product is employed to produce other pharmaceutically acceptable derivatives, e.g., salts.

Reactants

The starting material generally employed in the process of the invention include at least one epoxide reactant and at least one amine reactant.

The epoxide reactants useful herein include 3-(m-tolyloxy)-1,2-epoxypropane (II) and those chemically equivalent forms thereof in which the substituents present do not significantly hamper the reactively of the epoxide with compound III or its chemical equivalents. The epoxide reactant used herein may be obtained from commercial sources.

Alternatively, the epoxide reactant can be prepared by reacting one or more suitable hydroxy-substituted aromatic compounds, i.e., phenols, with one or more halogen-containing epoxy compounds. A typical reaction would involve the reaction of a cresol, e.g., m-cresol, and an epihalohydrin, e.g., epichlorohydrin, under suitable conditions. Suitable conditions for the preparation of the epoxide reactant are well known in the art.

Suitable amine reactants are generally amines bearing one or more organic substituents, at least one of which comprises a substituted phenyl alkylene moiety. Preferred amines are monoamines having disubstituted phenyl alkylene groups as substituents. One highly preferred class of amines are those containing 3,4-dialkoxyalkylene groups, with beta-3,4-(dimethoxyphenyl) ethylamine being exemplary.

Following the preparation of the Bevantolol, one or more reagents can be added to yield salts or other acid-addition products. Useful salt-producing agents include mineral acids, with hydrogen halides, especially hydrogen chloride, preferred.

One preferred derivative of Bevantolol which can be made in accordance with the invention is the pharmaceutically active substance Bevantolol hydrochloride, i.e.:

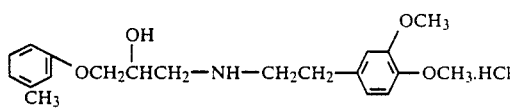

For all of the reactions described herein, the reactants are supplied in approximately stoichiometric quantities. However, excesses of one or more can be employed.

It is generally preferred that step (1) be carried out using little or no excess epoxide or amine reactant i.e., using stoichiometric or equimolor amounts. The use of an excess of either reactant produces undesirable —and often difficultly separable—by-products. The use of excess epoxide reactant can yield a bis (hydroxyalkylated) product. The use of excess amine, while less deleterious than the use of excess epoxide, can result in the production of contaminants which can hamper recovery operations.

Reaction Conditions

It is essential to the efficiency of the instant process that the initial contacting of epoxide and amine reactant take place at a temperature lower than room temperatures, i.e., about 25° C. or less. The use of relatively low temperatures during the initial phase of the reaction dramatically improves product yields. While temperatures of about 0° C. to about 20° C. are operable, it is generally preferred to operate, in the initial reaction stage, at temperatures of about 5° C. to about 15° C., with temperatures of about 5° C. to about 10° C. highly preferred.

The length of time for which various phases of the overall process are carried out can vary a great deal. Reaction parameters such as reaction times, pressures, etc. depend upon the nature of the specific reactants, and upon such factors as the type(s) of reaction vessel(s) employed, and the method of recovery to be employed.

Generally, the overall time needed for the principal reaction—i.e., "Step 2" under "The Invention," above—ranges from about 5 minutes to about 20 hours.

Typically the low temperature contacting and reaction phase takes place for about 5 to about 15 hours, with time periods of about 10 hours highly preferred.

After the initial reaction phase, the product mixture is seeded by adding Bevantolol free base. The quantity of base added can be determined by routine experimentation. Generally, a quantity or incremental quantities of seeding agent are employed, with the total amount added being in excess of the quantity needed to start crystallization of the Bevantolol in the product mixture. Useful total quantities of free Bevantolol or other seeding agent lie between about 0 and about 1% by weight, based on the total weight of the reaction product, with about 0.001 weight % to about 0.008 weight % preferred and 0.005 weight % highly preferred.

When seeding agent is added in increments, the use of several increments, with additions at intervals of one to several hours can be employed. Generally, about 2 to about 5 increments are added, with the use of 3 increments made in 2 hour intervals highly preferred. Seeding can be carried out over short or extended periods of time until it is completed. Seeding is completed when seed remains substantially undissolved, i.e., until seed no longer dissolves. Bevantolol hydrochloride and/or other seeding additives may replace some or all of the Bevantolol to be added.

Following the addition of the seeding agent conventional recovery procedures can be employed. One preferred method calls for the addition of hexane or another suitable non-solvent diluent to produce a slurry. The slurry is stirred and heated during or after the addition of the diluent. After moderate heating, i.e. to a temperature on the order of 25° C, the slurry is collected via filtration, and subjected to vacuum drying and/or other suitable techniques.

The solid product can be used as such or it can then be reacted with one or more suitable chemicals to produce other pharmaceutically acceptable derivatives, e.g., salts, thereof. Purification via, e.g., recrystallization, can be carried out before and/or after the derivative is produced.

EXAMPLES

The following examples will serve to further illustrate the invention.

Example 1

Preparation of 3-(m-tolyloxy)-1,2-epoxypropane

To a solution of 50 g (1.25 mol) of NaOH in 1200 ml H$_2$O was added 108 g (1 mol) of m-cresol freshly distilled and at 15° C. in one lot 117ml (1.5 mol) of epichlorohydrin. The emulsion was stirred at room temperature for 16 hours in a creased flask. The product was taken up in 1000 ml of toluene and washed with 500 ml water. Distillation yielded 135.7 g = 82% of product, bp 61° C. (0.05 mm).

Example 2

Preparation of Bevantolol Hydrochloride in Accordance with the Invention

To a suitable reactor under a nitrogen blanket is added 13.7 kg of beta-(3,4-dimethoxyphenyl) ethylamine. The amine is cooled to 5° C. and 12.5 kg of 3-(m-tolyloxy) 1,2-epoxypropane is added maintaining the temperature between 5–10° C. After 10 hours, the mixture is seeded with Bevantolol free base; seeding is repeated approximately every 2 hours until it is evident that crystallization has started. After stirring for 48 hours at 10° C., 26L of hexane is added. The temperature is raised to 25° C. and stirring is continued for 48 hours. The slurry is filtered and the collected solid is dried under vacuum.

The product is dissolved in 60L of isopropyl alcohol and the solution is filtered. The reactor and filter are rinsed with 186l of isopropyl alcohol and 2.7 kg of anhydrous hydrogen chloride is added to the combined filtrate. The batch is heated to reflux for 2 hours. The temperature is adjusted to 65° and the solution is seeded with Bevantolol hydrochloride crystals. The mixture is held at this temperature with stirring until a heavy sand-like slurry is present. The mixture is allowed to cool to ambient temperature without stirring or artificial cooling. It is then cooled to 20° C. The slurry is centrifuged and the product rinsed with isopropyl alcohol until the filtrate is colorless. After being vacuum dried at 50–55° C. the product is milled if necessary; yield of Bevantolol hydrochloride 22.7 Kg (78.6%).

COMPARATIVE EXAMPLES

Example 3* ,6

A mixture of 40.1 g (0.2 mol) of 1-chloro-3-m-tolyloxy-2-propanol and 72.4 g (0.4 mol) of 3,4is heated at 95–100° C. for 18 hours, cooled and then stirred with ethyl acetate. Insoluble 3,4-dimethoxyphenethylamine hydrochloride is removed by filtration. The filtrate is washed with water, dried, and evaporated to give a residue of 1-[(3,4-dimethoxyphenethyl)amino]-3-m-tolyloxy-2-propanol.

The hydrochloride is obtained by dissolving this free base in 2-propanol and adding a slight excess of hydrogen chloride in 2-propanol. The insoluble hydrochloride salt is collected on a filter, washed with diethyl ether, and dried; mp 137–138 ° C. following crystallization from acetonitrile, yield 44.4 grams, 58% based on the starting alcohol or 29% when based on the starting amine.

Example 4** ,6

A mixture of 8.2 g (0.05 mol) of 1.2-epoxy-3-m-tolyloxypropane and 9.05 g (0.05 mol) of 3,4-dimethoxyphenethylamine is heated at 95° C.–100° C. for one hour, cooled, and then stirred with ether. The insoluble product is collected on a filter. It is 1-[3,4-dimethoxyphenethyl) amino]-3-m-tolyloxy-2-propanol.

The hydrochloride is obtained by dissolving this free base in 2-propanol and adding a slight excess of hydrogen chloride in 2-propanol. The insoluble hydrochloride salt is collected on a filter washed with diethyl ether, and dried; mp 137–138° C. following crystallization from acetonitrile. Yield variable, but does not exceed 50%.

Example 5

A solution of 16.4 g (0.1 mol) of 3-(m-tolyloxy)-1,2-epoxypropane and 18.1 g (0.1 mol) of 3.4-dimethoxyphenethylamine in 50 ml of toluene was allowed to stand at room temperature for two days. The reaction mixture was diluted with 100 ml of toluene, washed with 2×25 ml portions of water, the toluene was evaporated, the crude product dissolved in 250 ml ethyl acetate (or 70 ml 2-propanol) and anhydrous HCl introduced with cooling. The product was filtered, washed with 100 ml ethyl acetate and dried at 70° C. to give 184 = 48% of crude product, mp 130–132° C. Recrystallization from acetonitrile gave 16.6 g=43.5% of product with mp 137-138° C.

Reasonable variations, such as those which would occur to a skilled artisan, can be made herein without departing from the scope of the invention.

What is claimed is:

1. In a process for preparing 1-[3,4-dimethoxy-phenethyl)amino]-3-(m-tolyloxy)-2-propanol (I)

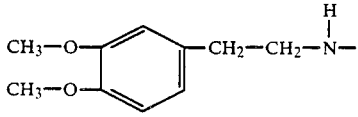

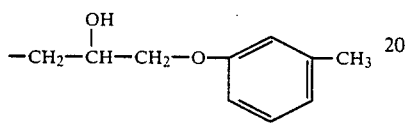

which comprises the reaction of 3-(m-tolyloxy)-1,2-epoxypropane

II

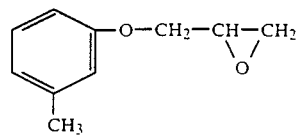

with beta-(3,4-dimethoxyphenyl) ethylamine (III)

III

CH$_3$O—⟨phenyl⟩—CH$_2$—CH$_2$—NH$_2$
CH$_3$O— the improvement which comprises:
  (1) contacting compounds II and III in stoichiometric amounts at a temperature from about 5° C. to about 10° C.;
  (2) adding a minor amount of a seeding agent until crystallization occurs;
  (3) heating the crystallized mixture to a temperature of at least about 25° C. until the reaction is substantially complete;
  (4) isolating the free base, and converting the free base to a pharmaceutically acceptable salt thereof.

* * * * *